US009539106B2

(12) United States Patent
Boehm et al.

(10) Patent No.: US 9,539,106 B2
(45) Date of Patent: Jan. 10, 2017

(54) EXPANDABLE IMPLANT FOR THE SPINAL COLUMN

(71) Applicants: Heinrich Boehm, Weimar (DE); Andreas Burger, Tuttlingen (DE); Gerd Widmaier, Tuttlingen (DE); Klaus Wenzler, Frittlingen (DE)

(72) Inventors: Heinrich Boehm, Weimar (DE); Andreas Burger, Tuttlingen (DE); Gerd Widmaier, Tuttlingen (DE); Klaus Wenzler, Frittlingen (DE)

(73) Assignee: Heinrich Boehm, Weimar (DE)

( * ) Notice: Subject to any disclaimer, the term of this patent is extended or adjusted under 35 U.S.C. 154(b) by 9 days.

(21) Appl. No.: 14/205,647

(22) Filed: Mar. 12, 2014

(65) Prior Publication Data

US 2014/0288652 A1  Sep. 25, 2014

(30) Foreign Application Priority Data

Mar. 12, 2013 (DE) .......................... 10 2013 102 451

(51) Int. Cl.
A61F 2/44 (2006.01)
A61F 2/46 (2006.01)
A61F 2/30 (2006.01)

(52) U.S. Cl.
CPC ............... *A61F 2/4465* (2013.01); *A61F 2/44* (2013.01); *A61F 2/442* (2013.01); *A61F 2/4611* (2013.01); *A61F 2002/30405* (2013.01); *A61F 2002/30523* (2013.01); *A61F 2002/30556* (2013.01); *A61F 2002/30579* (2013.01); *A61F 2002/30601* (2013.01); *A61F 2002/30774* (2013.01); *A61F 2002/30784* (2013.01); *A61F 2002/30843* (2013.01); *A61F 2002/4627* (2013.01)

(58) Field of Classification Search
CPC ................... A61F 2/4425; A61F 2002/30578; A61F 2002/30579
USPC ............ 606/246, 248, 249; 623/17.11–17.16
See application file for complete search history.

(56) References Cited

U.S. PATENT DOCUMENTS 5,236,460 A    8/1993 Barber
8,192,495 B2 *  6/2012 Simpson .................. A61F 2/44
                                                  623/17.15

(Continued)

FOREIGN PATENT DOCUMENTS

EP      1415622 A1   5/2004
WO   2009064787 A2   5/2009

*Primary Examiner* — Ellen C Hammond
*Assistant Examiner* — Christina Negrellirodrigue
(74) *Attorney, Agent, or Firm* — Kriegsman & Kriegsman

(57) ABSTRACT

An expandable implant with an upper plate and a lower plate which serve for anchoring on/in the vertebral support surfaces, and at least two gears for the expansion of the implant, which are coupled to each other via toothed wheels. Each gear includes threaded spindles and threaded sleeves, the threaded spindles are connected rigidly to the upper plate, and the threaded sleeves are mounted rotatably in the lower plate, and on one gear a drive shaft is provided, which is connected rigidly to the one threaded sleeve, and wherein a force acting on the drive shaft of an operating instrument can be transferred to the gear by the drive shaft, and the implant includes a mechanism for rigidly securing, screwing or fixing the operating instrument on the implant. The invention also relates to an operating instrument for an implant.

14 Claims, 9 Drawing Sheets

(56) References Cited

U.S. PATENT DOCUMENTS

Figure 1:
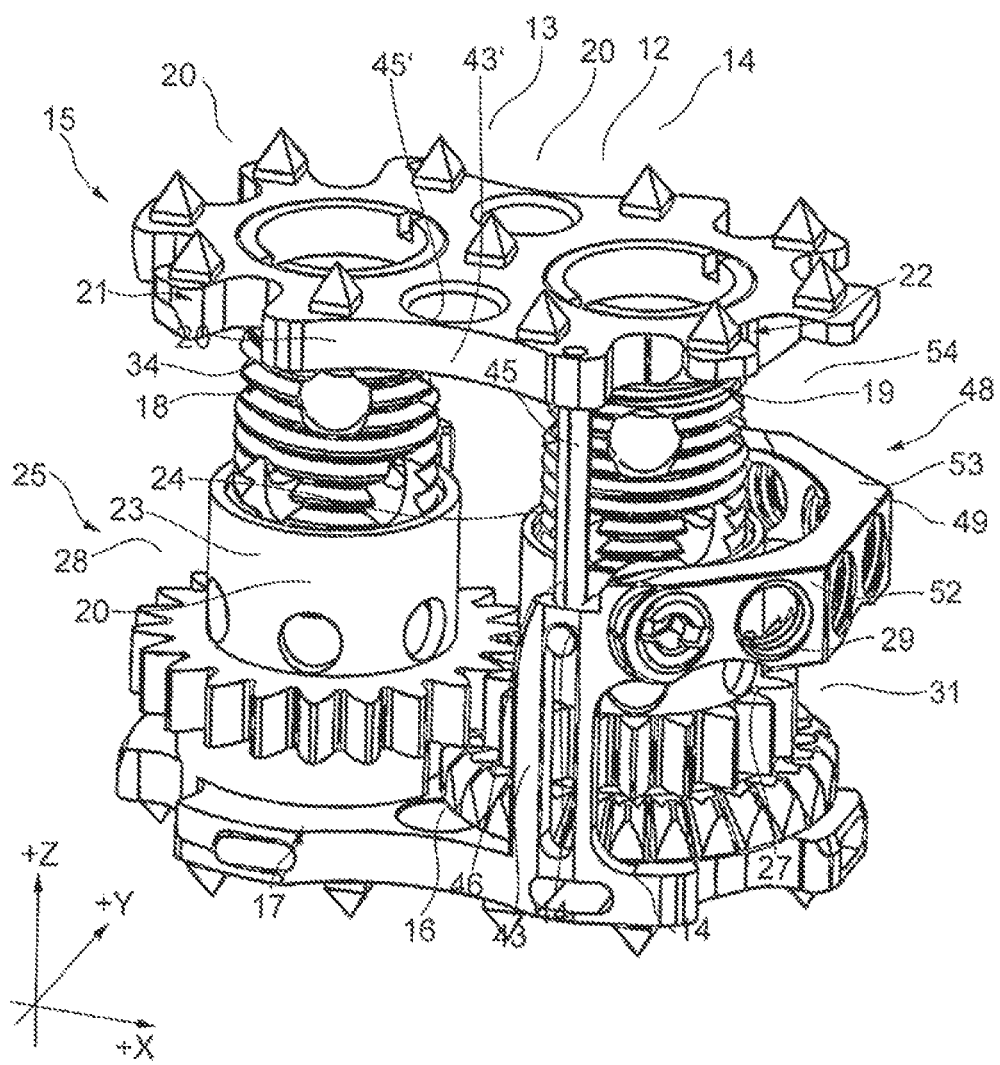

| | | | |
|---|---|---|---|
| 8,303,663 B2 * | 11/2012 | Jimenez | F16H 25/2056 623/17.16 |
| 8,591,587 B2 * | 11/2013 | Refai | A61F 2/44 623/17.15 |
| 2011/0160861 A1 | 6/2011 | Jimenez et al. | |
| 2012/0179255 A1 | 7/2012 | DeFalco et al. | |

* cited by examiner

EXPANDABLE IMPLANT FOR THE SPINAL COLUMN

The present invention relates to an expandable implant, in particular the invention relates to an expandable height-adaptable implant for the lumbar and thoracic spine, which can serve as a replacement for vertebral bodies and/or intervertebral disc spaces in stiffening operations.

Such lumbar and thoracic implants are used intercorporeal fusion (stiffening of the vertebral bodies). However, an intracorporeal use is also possible in principle.

In the configuration as a vertebral body replacement, the implant can be used on destroyed areas or formational defects of any kind, e.g. tumours, vertebral fractures, late sequelae following vertebral factures, and also infections or congenital malformations of one or more vertebral bodies.

In the configuration as an intersomatic cage or expandable cage, the implant can be used to restore the anterior column of the row of vertebrae in the context of stiffening procedures. Here, areas of application are degenerative diseases of the spinal column, segment malpositioning and segment instability of a very wide variety of causes.

Generally, the intervertebral space is first of all excavated from the back or from the direction of the thoracic or abdominal cavity; in vertebral body replacement, the vertebral body is removed and the implant is then inserted into the resulting space in order to correct the position and also to serve as a spacer for mechanically stable connection between the adjacent spinal column sections.

It has proven advantageous to design such implants in the form of a cage such that, for example, bone substance or bone replacement substances can be introduced into the interior of the cage in order to accelerate the process of incorporation. The fusion of the cage can be permitted or accelerated in this way.

Cages that can be expanded via an expansion mechanism after they have been inserted into the spinal column defect have the advantage of being able to be implanted in a technically simpler way that is gentle on the anchor vertebrae. On the one hand, the implant is firmly clamped and fixed by the stepless expansion. On the other hand, it permits individual positional corrections of the adjacent vertebrae, in order to restore normal geometric relationships by creation of lordosis of the lumbar spine or correction of an increased thoracic kyphosis.

Except in cases of malignant tumours, the aim is to allow endogenous bone tissue to grow through the implant or the reconstructed spinal column section. For this reason, such implants preferably have apertures.

Depending on their design, cages not only ensure mechanical stability of the corporectomy defect and structural integrity of the intervertebral space during the osseous fusion process, but also protect the spinal cord from moving bone fragments.

A general problem of the known implants is that the implants, after they have been fitted, are liable to sink into the adjacent vertebrae, as a result of which the position of the vertebrae relative to each other and the overall statics may be disrupted. This can occur particularly in cases of reduced calcium salt content (osteoporosis) of the vertebral bodies.

Cylindrical implants are known which have a screw thread on the cylinder surface. These implants are screwed horizontally into the intervertebral space after the bottom plate and top plate of the vertebral bodies have firstly been eroded using drilling instruments, that is to say have been partially removed. A disadvantage of these cylindrical implants is that they have a relatively small bearing zone and exhibit quite considerable sinking into the vertebral bodies and become jammed.

EP 1 415 622 A1 discloses expandable implants of a more or less parallelepipedal basic shape, which have two branches which are connected to each other at one end, wherein the branches can be expanded by a slide arranged between the branches, which slide supports the branches, in the expanded state, over their entire horizontal width and locks them in the end position. Although these implants are distinguished by a greater bearing surface on the end plate of the adjacent vertebra, the nature of the expansion is very limited for design-related reasons and always angle-shaped. On account of the then often unavoidable punctiform loading, they also often sink substantially into the adjacent vertebrae and thus lose their expanding or correcting function. In addition, implantation of such cages from the side of the spinal column is not possible for design-related reasons and is strictly limited to a dorsal implantation direction or, in rare cases, strictly to an anterior implantation direction. The use as a vertebral body replacement is impossible with both of the aforementioned models.

US 2012/017955 A1 discloses an expandable implant comprising four gears, of which two in each case are coupled to each other by toothed wheels. Above and below the toothed wheels, the gears each have a threaded spindle with a different direction of rotation, such that, when the toothed wheel is actuated, the upper and the lower thread are unscrewed simultaneously from the upper and lower plate and therefore the upper plate is expanded relative to the lower plate, and the implant is compressed when the threads are simultaneously screwed into the plate. The implant is of a complex construction and, with a large overall volume, allows only a slight lift. This implant does not allow bone to grow through. A further disadvantage is the cylindrical shape of the implant with the circular plates that serve for anchoring on/in the vertebral support surfaces. When positioning such implants, the implant comes to lie straight in the centre of the vertebral support surface, i.e. the least hard area of the entire vertebral support surface, with the result that the implant sinks. On account of the cylindrical shape and the engagement of the operating instrument in the cylinder centre, it is also not possible, in the case of a dorsal implantation, to pivot the implant past the nerve roots and into the correct position using the operating instrument. The implant is therefore unsuitable for dorsal, dorso-lateral or TLIF implantation.

U.S. Pat. No. 5,236,460 discloses expandable telescopic implants. The outer implant body, which is tubular, has an axial bore, in which the inner implant body is guided in a sliding movement. Plates with spikes for anchoring are provided at the upper end and lower end of the implant bodies. The expansion of the implant takes place hydraulically via a liquid or a hardenable resin. For this purpose, the outer implant body has an opening for entry of the fluid, which fluid then passes into a cavity in the lower end of the inner implant body and pushes the latter up axially in a sliding movement. The implant is screwed onto the vertebral bodies via a special bracket device, which is screwed onto the upper platform.

US 2011/0160861 A1 teaches an expandable implant with a more or less rectangular basic shape and with two gears. The gears are coupled via a drive rod that passes through the bottom in the longitudinal direction. The insertion instrument is screwed in the longitudinal direction onto the short sides of the implant, such that the implant can be used in particular for lateral or XLIF implantation. This implant, is not suitable for the TLIF technique (transforaminal/transarticular lumbar interbody fusion), since it cannot be brought round the nerve roots into the optimal position. When using the PLIF technique, this implant has to be implanted via two accesses. As regards the ALIF technique, i.e. anterior implantation through the abdomen, this implant can be brought only from the side and, consequently, not to the optimal position. A further disadvantage is that the implant does not allow bone to grow through.

WO 2009/064787 discloses expandable implants with a dual telescopic adjustment mechanism, which implants have an upper plate and lower plate for anchoring on the vertebral support surfaces. The adjustment mechanism is coupled via toothed wheels, i.e. a rotation movement is transferred from one toothed wheel to the other toothed wheel and thus from one adjustment mechanism to the other adjustment mechanism. The adjustment mechanism in each case comprises a thread, which is connected to the upper plate and lower plate, and two central drives, by means of which the implant can be expanded. According to said document, the actuation is intended to take place via a rod with a bevel gear transmission in a manner not explained in detail.

This implant is suitable as an intervertebral, disc replacement. On account of the larger surface of the upper and lower plates, the risk of secondary positional changes and of sinking is minimized. However, the maximum lift that can be obtained with this adjustment mechanism is relatively small. A further disadvantage is that these implants have not hitherto been able to be introduced, expanded and fixed easily by a minimally invasive technique, that the structure of the implant is complicated, and that it also does not allow bone to grow through.

The object of the invention is to make available an implant that is expandable in the body and thus has a correcting function for stiffening the intervertebral space or after the removal of vertebral bodies, which implant is easy to handle and operate and can also be safely implanted using a minimally invasive technique, and which ensures that no bone fragments can get into the spinal canal and there narrow or damage the spinal cord.

This object is achieved by an implant having the features of Claim 1 and by an operating instrument having the features of Claim 11.

The implant according to the invention, which has an upper plate and a lower plate which serve for anchoring in the vertebral support surfaces, and at least two gears for the expansion of the implant, which are coupled to each other, further comprises a drive shaft on the one gear, by means of which a force acting on the drive shaft of an operating instrument can be transferred to the gear. The expandable implant further comprises means for securing, screwing or rigidly fixing the operating instrument.

In this way, the implant can be rigidly fixed on the operating instrument and also, at the same time, the gear can be driven with the same operating instrument, and therefore the implant can be expanded via the coupling of the two gears.

This permits simple handling of the implant during the operation, since only one operating instrument is needed, which permits both the fixing on the implant and also the expansion, and also the fixing of the expansion position as will be described in detail below.

The drive shaft, which is rigidly connected to the threaded sleeve, is preferably a ring gear or a taper ring, to which a rotation movement can be transferred by a bevel wheel gear (described later) of the operating instrument.

The ring gear extending radially outwards on the outer curved surface of the threaded sleeve is easily accessible from the outside for the bevel wheel gear of the operating instrument. By virtue of the operating instrument being secured rigidly on the implant in the manner described in detail below, the area around the bevel wheel gear is also screened off such that, upon actuation of the operating instrument, squeezing-in of the tissue and obstruction of the function of the bevel gear transmission are avoided.

For easy operation and implantation, it is also necessary that the operating instrument can be secured rigidly on the implant. For this purpose, according so the invention, the implant has means for securing, screwing or otherwise rigidly fixing the operating instrument. The connection between implant and operating instrument must of course be releasable. Preferably, the operating instrument comprises a screw thread (outer thread), which can be screwed into a corresponding bore in the implant and which can be removed again after the positioning and expansion have been completed. However, the connection can also be made in other ways.

Since the operating instrument engages with the drive shaft (bevel wheel gear) on the drive shaft (ring gear) of the threaded sleeve, and the tightening shaft of the operating instrument is screwed into the bore of the implant and the distance between the screw thread of the tightening shaft and the bevel wheel gear in the operating instrument is constant, it is also necessary that the distance between the bore for receiving the screw thread in the implant and the ring gear is not able to change, i.e. the bores for receiving the screw threads in the implant must be rigidly connected to the plate in which the threaded sleeve with the ring gear is rotatably mounted.

By virtue of the dual adjustment mechanism, the expansion is initiated by two gears, and a jamming of the gear is thereby avoided. Another essential advantage of the dual adjustment mechanism is that, as a result of the dual expansion movement, the surface area of the upper plate and lower plate is also increased, and therefore the pressure acting on the vertebral bodies per surface area element can be reduced. The reduction of the surface pressure additionally reduces the undesired sinking of the implant. Of course, the adjustment mechanism can also have more than two gears, for example three or four.

By virtue of the design of the gear elements with a threaded sleeve and a threaded spindle and the coupling thereof, operation is made easier and a smooth expansion movement is achieved.

Through the interaction of threaded sleeve and threaded spindle, the necessary distance between the upper plate and lower plate in the desired expansion position can be adjusted with precision and in a simple manner.

The coupling is effected via toothed wheels, which are rigidly connected no the outer curved surfaces of the threaded sleeves, wherein in each case two toothed wheels on different threaded sleeves form a pair of toothed wheels.

Of course, the drive shaft of the operating instrument and the securing means of the operating instrument correspond to the corresponding shafts/securing means of the implant. Preferably, the operating instrument is screwed into bores, in particular threaded bores, of the implant, specifically with an outer thread at the proximal end of a tightening shaft.

The drive shaft of the implant is preferably designed as a bevel wheel gear, which is located at the proximal end of a rotation shaft. Rotation shaft and tightening shaft are arranged parallel to each other.

Preferably, the operating instrument has a retainer composed of tubes and holders, wherein the tubes serve to receive the tightening shafts and/or a screw instrument, and the rotation shaft is also guided in the retainer.

With the implant and operating instrument according to the invention, an implant is for the first time made available that can be employed universally, since it can be used for implantation in the supine, lateral and prone positions in the XLIF, ALIF and TLIF techniques, specifically also in implantation of the 4th or 5th lumbar vertebra. This is achieved by the fact that the implant has a plurality of differently oriented sub-portions (i.e. the surfaces of the sub-portions are not coplanar with each other), on which the operating instrument can be secured. Depending on the sub-portion on which the operating instrument is secured, it is possible to obtain a different angle between the longitudinal axis of the implant and the longitudinal axis of the operating instrument and, therefore, another orientation of the longitudinal axis of the implant with respect to the longitudinal axis of the operating instrument.

After the implant has been introduced into the intervertebral defect or corporectomy defect, expansion is carried out until mechanically stable anchoring and, if appropriate, positional correction have been achieved. The achieved expansion can be modified at any time during the operation, in order to carry out possible repositioning or to reverse an overexpansion of the spinal column segment by actuation of the bevel wheel gear on the operating instrument. Without actuation of the bevel wheel gear, however, the implant remains safely in the expanded position as a result of friction and, after the desired expansion has been reached, can then be secured by a closure pin.

On account of the stability of the implant afforded by the doubled columns, it is possible to choose the surface area, the angle degrees and also the surface configuration of the upper and lower plates relatively freely and thereby optimize the form it and counteract the undesired sinking of the implants.

The implant according to the invention is preferably made from pure titanium or a titanium alloy such as Ti$_6$Al$_4$, tantalum, Nitinol, a plastic such as polyether ether ketone (PEEK), or other materials that are suitable as implant materials.

The implant according to the invention is implanted as follows:

With the patient lying on his front, on his side or on his back, the intervertebral space is exposed via a dorsal or ventral abdominal or thoracic approach and is then completely excavated. If a vertebral body is to be removed, this procedure is repeated on the second adjoining intervertebral disc, and the corporectomy is then performed. Depending on the indication, either only parts of the vertebral body can be resected or all parts of the vertebral body can be removed from the spinal canal, including the posterior margin and, if appropriate, bone fragments from the spinal canal. The end plates of the anchor vertebrae then have cartilage removed and are roughened in order to stimulate growth of bone.

The implant chosen with a suitable size and shape is then introduced into the excavated defect by means of the operating instrument according to the invention, a combined holding, expanding and locking instrument, and is expanded. The geometry of the implant and of the operating instrument permits insertion from the front, from both sides, and also from the rear to the side of the spinal cord sac. The surgical approach can be conventional and open, but it can also be made using a minimally invasive technique. The advantage of a symmetrical introduction of relatively strong corrective forces is afforded particularly in the keyhole technique.

Since the size and configuration of the end plates can be combined relatively freely with the two extension bodies, a large support surface can likewise be used in osteoporosis, and a small one in cases of vertebral fractures where parts of the vertebral body can be preserved.

During the expansion, an edge optionally mounted on the inner cylinder leads to a trimming of the end plate of the anchor vertebra not required for the support and thus means that the end plate that is more difficult to access does not have so be trimmed in a separate work step.

The position is then monitored by intraoperative imaging, mostly by radioscopy. If the position of the implant is less than optimal, the expansion device is rotated in the opposite direction and the implant is thus closed together, repositioned and then expanded again.

The implant can be filled with bone (e.g. spongy bone) or other materials (calcium phosphate preparations). The reconstruction of the anterior column is thus complete. Combination with dorsal stabilization is highly recommended especially in she thoracolumbar and lumbar region. Depending on the quality of the bone and the loss of blood, the patient can be mobilized on the same day.

The invention is described in more detail below on the basis of an illustrative embodiment.

Figure 2:
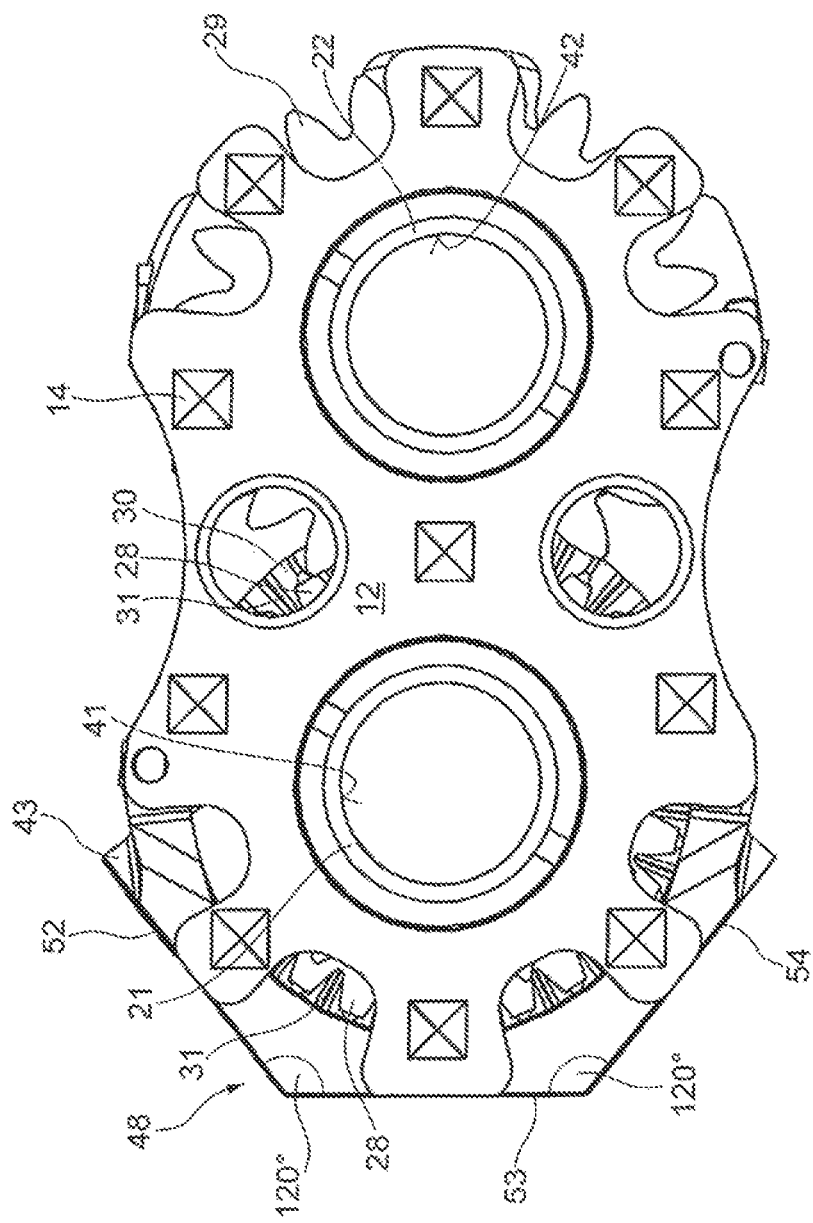
Figure 3:
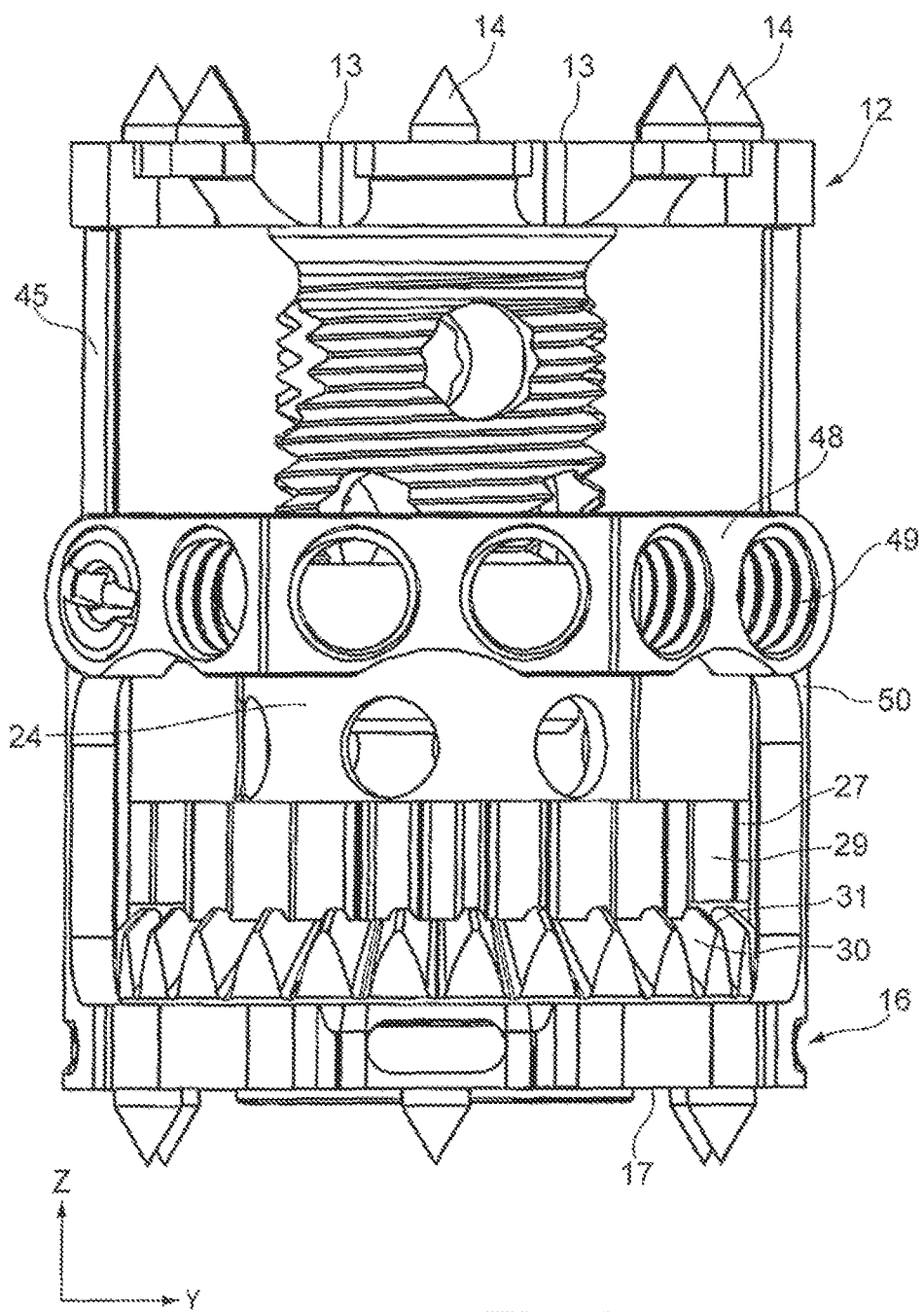
Figure 4:
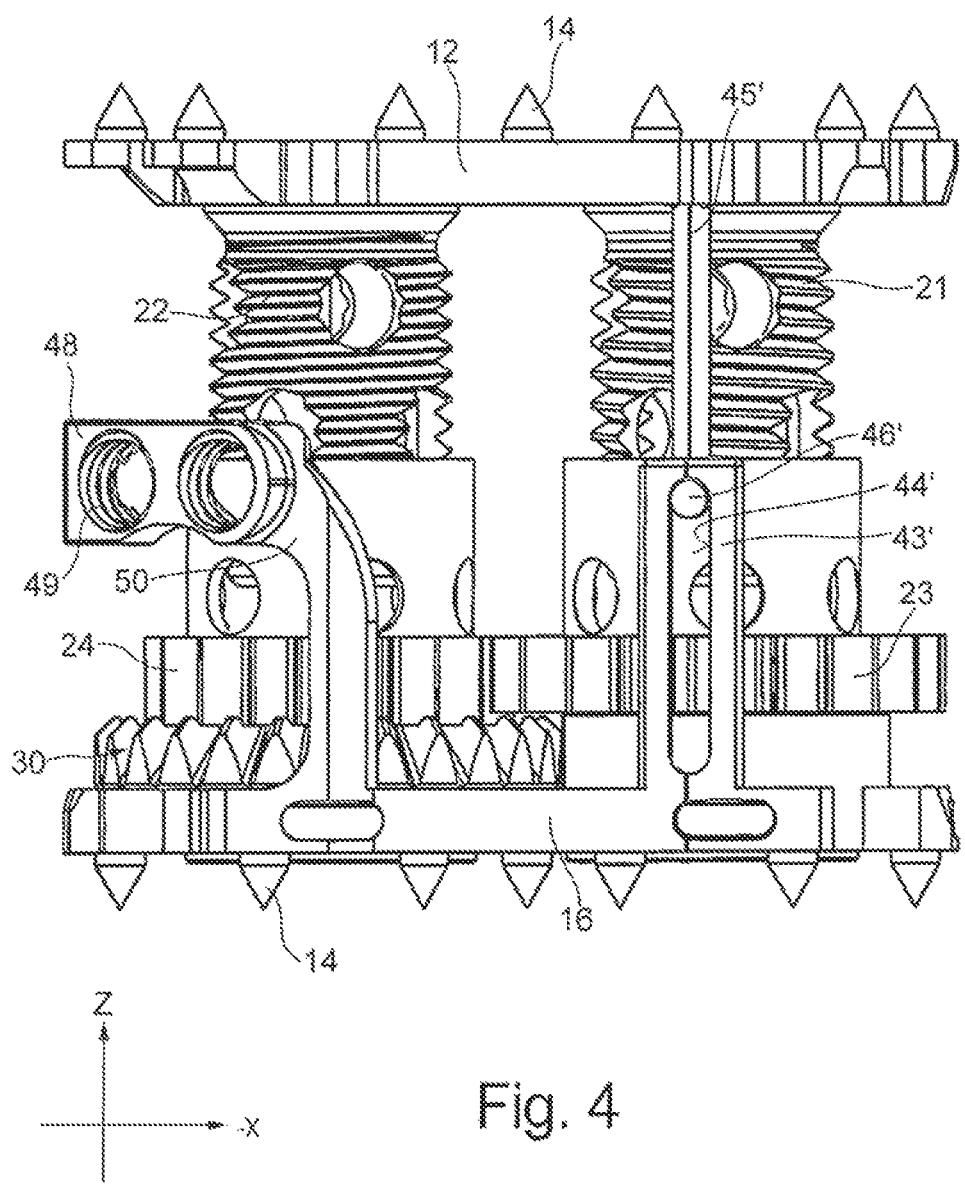
Figure 5:
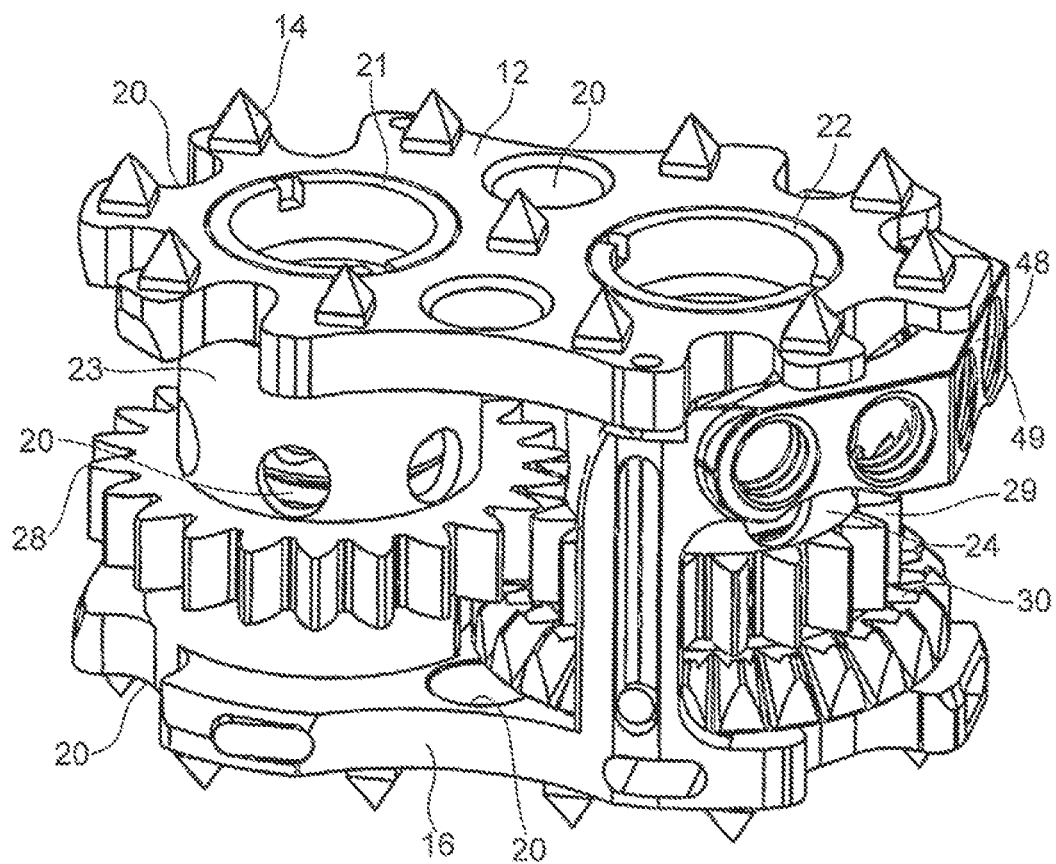
Figure 6:
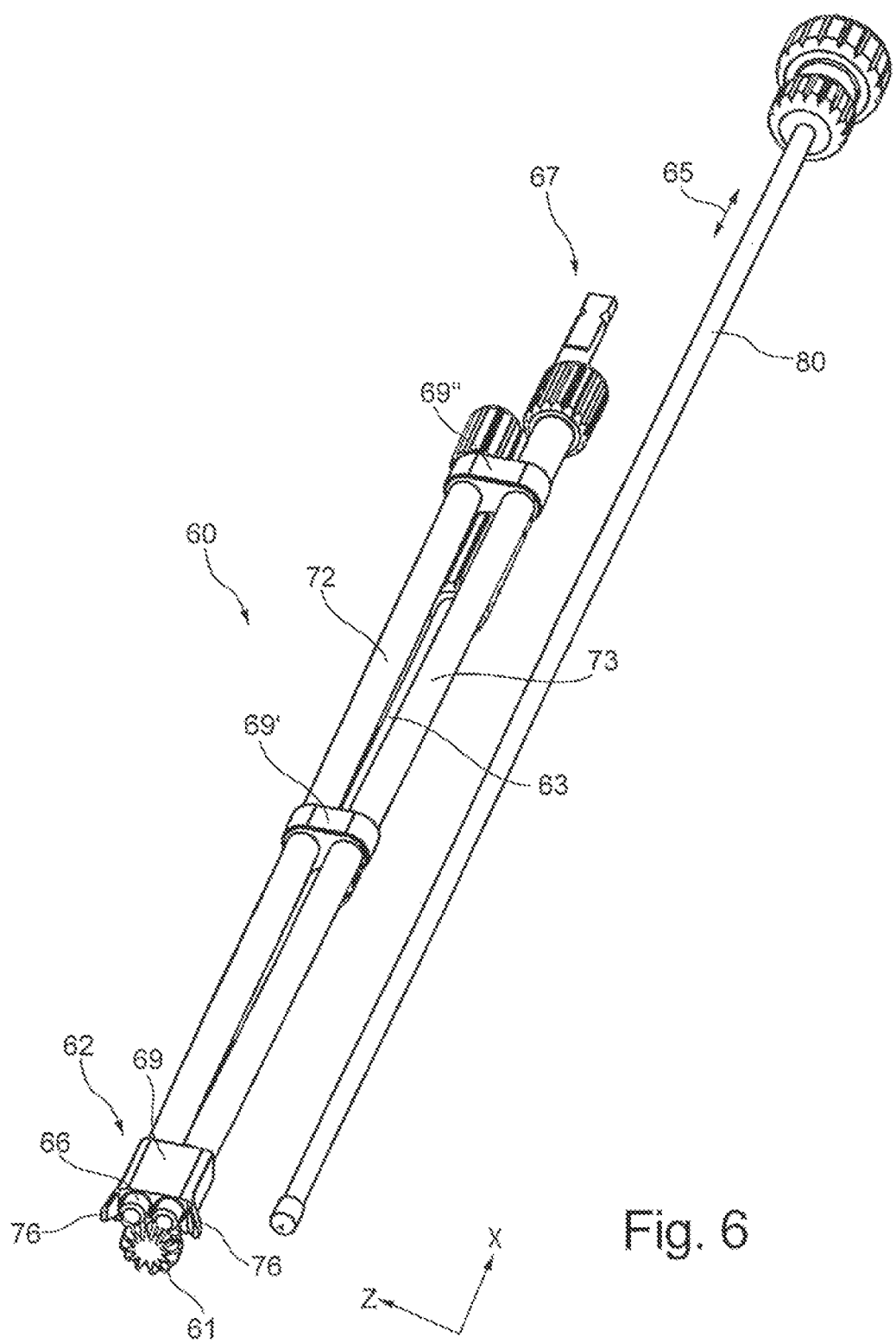
Figure 7:
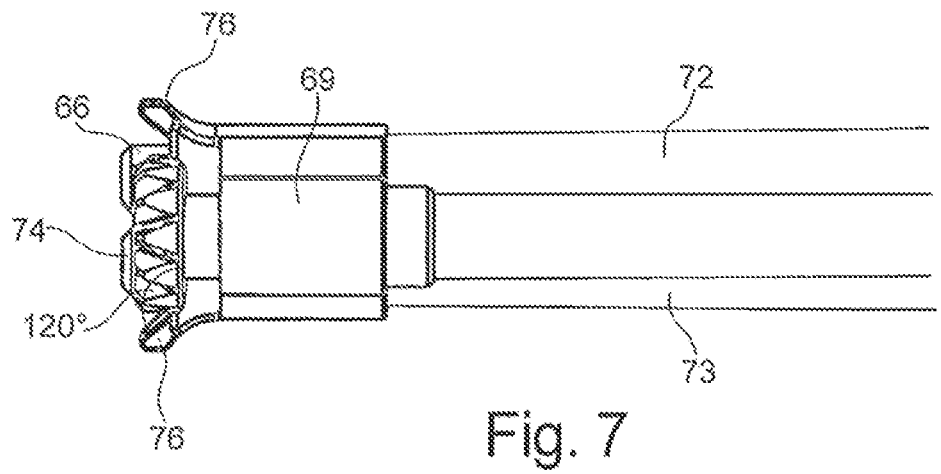
Figure 8:
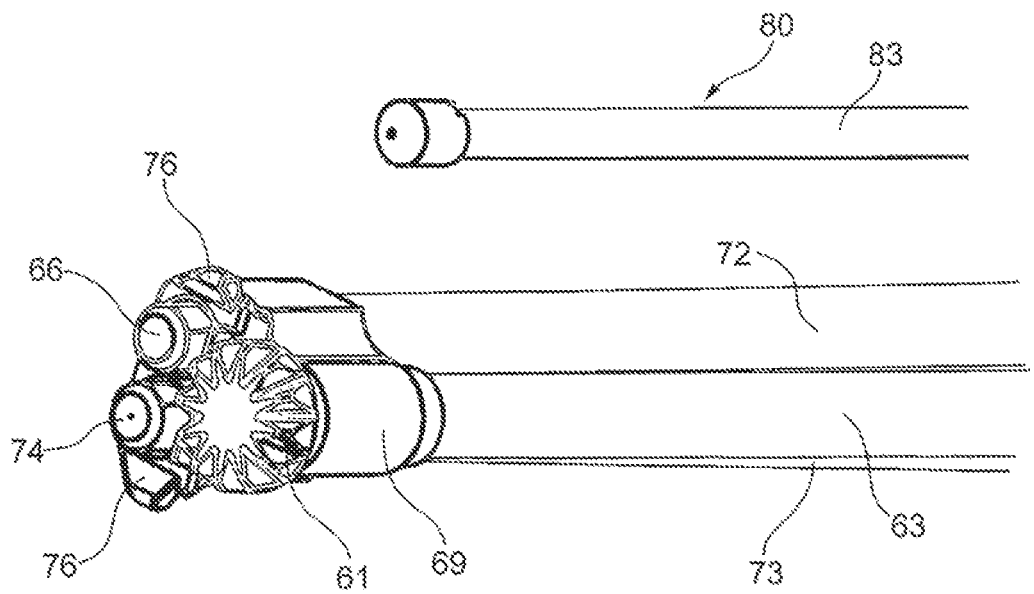
Figure 9:
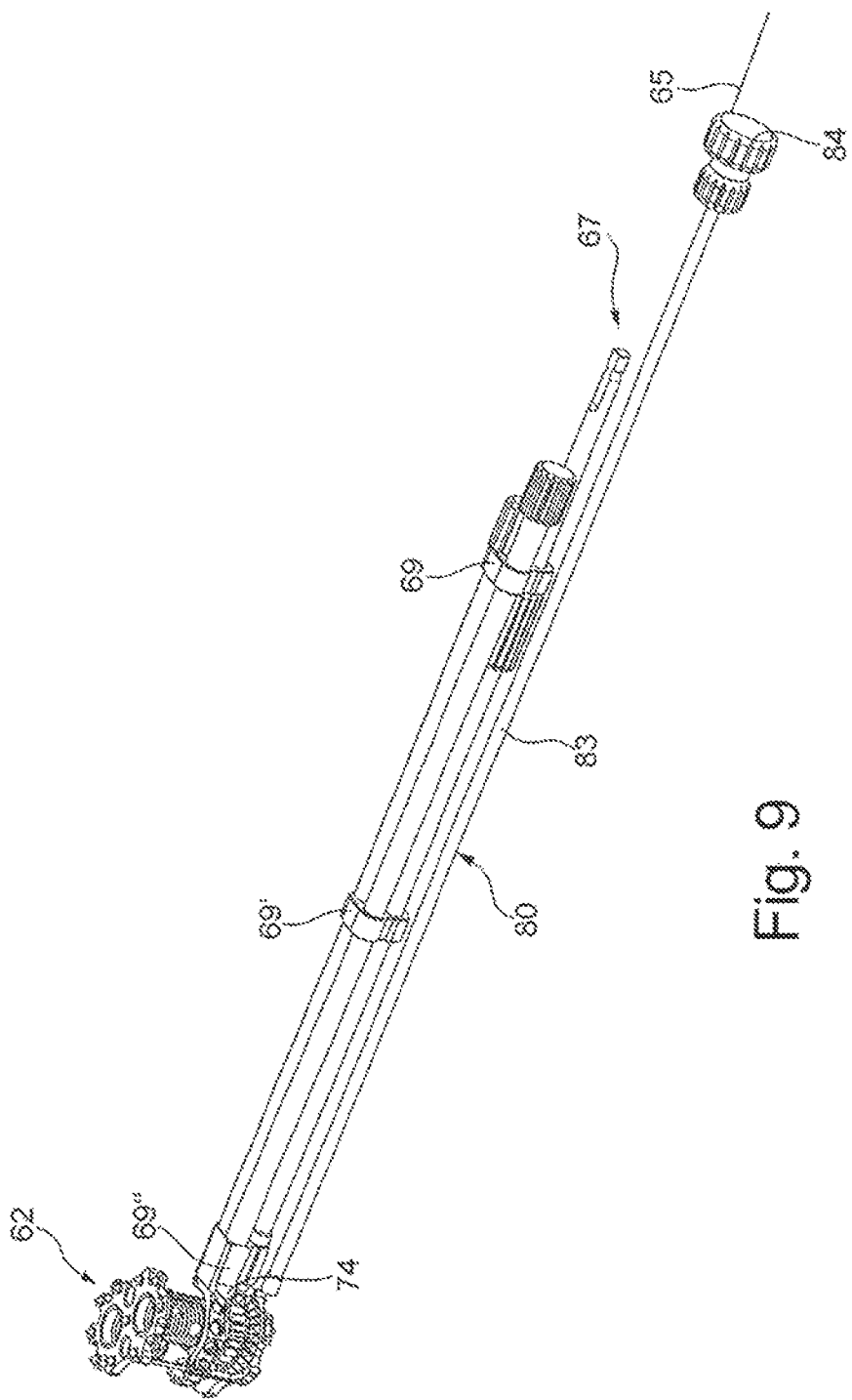
Figure 10:
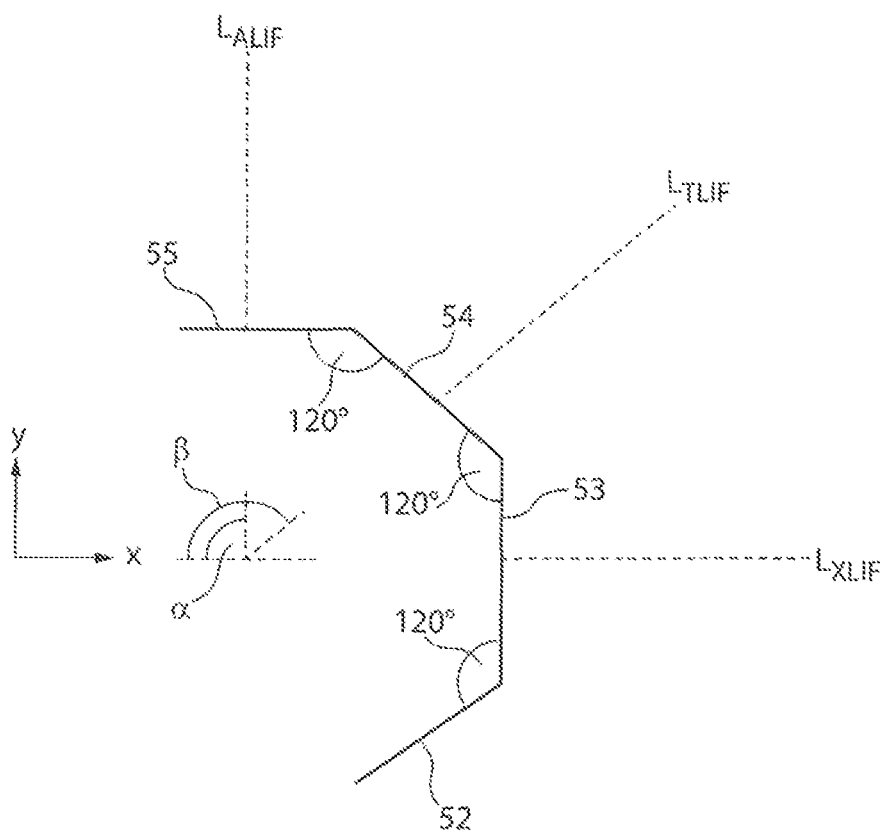

In the drawing:

FIG. 1 shows a perspective view of the implant according to the invention at maximum expansion, FIG. 2 shows a plan view of the implant from FIG. 1 from above, FIG. 3 shows a side view of the implant from FIG. 1 in the x direction, FIG. 4 shows a side view (xz direction) of the implant from FIG. 1, looking from behind (y direction), FIG. 5 shows the implant from FIG. 1, but in the non-expanded state, FIG. 6 shows the operating instrument according to the invention and the screw instrument 80 in a perspective view, FIG. 7 shows the side view of the proximal end of the instrument from FIG. 6, FIG. 8 shows the perspective view of the proximal end of the operating instrument from FIGS. 6 and 7, FIG. 9 shows the implant in the expanded state, with the operating instrument secured thereon, and FIG. 10 shows the plan view of another variant of the horizontal portion. 18 with four different sub-portions 52, 53, 54 and 55 at which the operating instrument can be screwed at different angles onto the implant.

The implant comprises an upper plate 12 and a lower plate 16, of which the outer faces 13, 17 are provided with spikes 14 that serve for anchoring on/in the vertebral support surfaces.

Between the upper plate 12 and the lower plate 16 there are two gears, by means of which the upper plate 12 is movable relative to the lower plate 16, i.e. the implant can be expanded.

The gears each consist of a threaded spindle 21, 22 and mating threads 23, 24, the mating threads 23, 24 being designed as threaded sleeves.

On the outer curved surfaces 34, 35, the threaded spindles 21, 22 have outer threads 18, 19. The outer threads 18, 19 of the threaded spindles 21, 22 are spaced apart from each other. The longitudinal axes of the threaded spindles 21, 22 extend parallel to each other and are rigidly connected to the upper plate 12, i.e. the two threaded spindles 21, 22 and the upper plate 12 with the spikes 14 form the upper implant part 15, which is in one piece.

The lower implant part 25 comprises the lower plate 16 with the spikes 14 and the two threaded sleeves 23, 24 that are mounted rotatably in the plate 16.

The inner curved surfaces 37, 38 of the threaded sleeves 23, 24 are provided with threads 39, 40, which form the spindle nuts for the outer threads 18, 19 of the threaded spindles 21, 22.

Each threaded sleeve 23, 24 also has, on its outer curved surface, a toothed wheel 28, 29. The toothed wheels 28, 29 on the threaded sleeves 23, 24 form a pair of toothed wheels and couple the rotation movement of the two threaded sleeves.

The threaded sleeves 23, 24 are mounted rotatably in the lower plate 16. When a rotation movement takes place on a threaded sleeve 23 (or 24), the rotation movement is transferred to the other threaded sleeve 24 (or 23) by the meshing of the pairs of toothed wheels 28, 29. These coupled toothed wheels have the effect that the expansion mechanism is driven with a dual adjustment mechanism.

Moreover, however, the rotation movement, on each threaded sleeve 23, 24 also has the effect that a displacement movement of the threaded spindles 21, 22 relative to the threaded sleeves 23, 24, and thus a displacement of the upper plate 12 relative to the lower plate 16, and thus an expansion of the implant, takes place.

In this way, the expansion of the implant, upon rotation of one of the two threaded sleeves, takes place in a smooth movement, and jamming of the threads is avoided.

The directions of rotation of the threaded spindles 21, 22 are different, likewise the directions of rotation of the threaded sleeves 23, 24. A rotation movement on one toothed wheel has the effect that the other toothed wheel rotates in the opposite direction, and therefore the threaded sleeves 23, 24 mounted rotatably but not vertically adjustably in the lower plate 16 also rotate in opposite directions, and, as a result of the different directions of rotation of the threaded spindles 21, 22, the upper plate 12 is lifted relative to the lower plate 16.

Located below the toothed wheel 29 is the drive shaft 30 (ring gear) of a bevel gear transmission which extends radially outwards from the toothing 27 of the toothed wheel 29. The external diameter of the ring gear 30 is greater than the diameter of the toothed wheel 29. Thus, the bevel wheel gear 61 of the operating instrument 60 can engage on the outer circumference of the ring gear 30 without impeding the movement of the toothed wheel 29.

Ring gear 30, threaded sleeve 24 and toothed wheel 29 form a rigidly interconnected unit. The toothing 31 of the ring gear 30 points in the direction of the upper plate 12, i.e. in the +z direction, and extends approximately at right angles to the toothing 27 of the toothed wheel 29, which extends in the xy direction.

By a rotation of the ring gear 30, the toothed wheel 29 is also rotated at the same time and therefore, via the coupling of the toothed wheels 28, 29, also the toothed wheel 28 and thus the two threaded sleeves 23, 24 connected to the toothed wheels, as a result of which the implant is expanded.

Parallel to the longitudinal axes (z direction) of the threaded sleeves and spindles 21, 23; 22, 24, a portion 43 connected rigidly to the lower plate 16 and likewise pointing in the direction of the upper plate 12 is provided with an oblong hole 44 in which a guide web 45 is guided, which guide web 45 is secured on the upper plate 12 and has a stop pin. 46 at its end. During the expansion, the guide web 45 slides upwards in the oblong hole 44 until the maximum expansion is reached and the stop pin 46 located at the end of the guide web 45 bears on the upper end of the oblong hole 44.

On the threaded sleeve 24 with the ring gear 30, a horizontal portion 48 with a plurality of threaded bores 49 is additionally provided on the portion 43 connected to the lower plate 16, into which threaded bores 49 it is possible to screw a corresponding screw thread 66 on the operating instrument 60 or screw plugs 78. For reasons of stability, the horizontal portion 48 with the threaded bores 49 is also rigidly connected to the lower plate 16 by a web 50 on the side lying opposite the portion 43 with the oblong hole 44.

Lower plate 16, portion 43, horizontal portion 48 with the bores 49 and web 50 form a rigid unit.

Six threaded bores 49 in total are provided on the horizontal portion 48. In the further variant of the horizontal portion 48 shown in FIG. 10 with four sub-portions 52 to 55, there are a total of eight bores 19 (not shown). The horizontal portion 48 consists of three sub-portions 52, 53, 54, wherein the end of the first portion 52 is adjoined in the xy direction by the second portion 53 at an angle of 120°, and the opposite end of the second portion 53 is adjoined in the xy direction by the third portion 54, again at an angle of 120° (cf. FIG. 2). This outer configuration of the horizontal portion 48 serves for the simple positioning of the operating instrument 60, as will be described below.

The various differently oriented threaded bores 49 allow the physician to secure the implant in the desired orientation on the operating instrument 60 and to insert it in this position from the desired side.

There are two threaded bores 49 on each one of the three sub-portions 52, 53, 54. The threaded bores 49 serve both for the securing of the screw thread 66 on the tightening shaft 72 of the operating instrument 60 and also for the fixing of the expansion position by the screw plug 78. The distance between two threaded bores 49 on a sub-portion corresponds to the distance between the proximal ends of the two receiving tubes 70, 71 of the operating instrument 60, by which the implant is temporarily screwed onto the operating instrument 60, and by which the remaining fixing of the expansion position takes plane by means of the screw plug 78 with the screw instrument 80.

If the operating instrument 60 is screwed onto the implant such that it bears on the portion 54 (or 52), the angle between the longitudinal axis of the operating instrument 60, shown in FIG. 10 as $L_{TLIF}$, and the longitudinal axis of the implant is β=125°. In this securing position, in which the longitudinal axis of the implant and the longitudinal axis of the operating instrument enclose an obtuse angle, the implant can be easily implanted from behind in the TLIF technique (the patient lying in the prone position). In particular, on account of the obtuse angle β, the implant can be pushed round the nerve roots into the desired position between the vertebral bodies without damaging these. Moreover, by virtue of the securing angle, the implant can also be brought safely into not just any position but also into the optimal position, which is not possible, purely for geometric reasons, with the previously known implants extending in the longitudinal direction of the operating instrument.

By contrast, if the operating instrument is screwed onto the implant at the portion 53, the operating instrument engages on the narrow side of the implant, i.e. the longitudinal axis of the implant, shown in FIG. 10 as $L_{XLIF}$, and the longitudinal axis of the operating instrument extend parallel to each other. In this securing position, implantation can be performed using the XLIF technique (extreme lateral interbody fusion) with the patient in the lateral position, as may be necessary particularly in respect of the 4th lumbar vertebra.

In a further variant of the horizontal portion 48 shown in a plan view in FIG. 10, the portion 54 is adjoined at an angle of 120° by a further portion 55 which, like the other portions 52, 53 and 54, similarly has two bores 49. The portion 55 extends parallel to the longitudinal axis of the implant, i.e. in the x direction. If the operating instrument is secured on the portion 55, the longitudinal axis of the operating instrument 60, shown in FIG. 10 as $L_{ALIF}$, and the longitudinal axis of the implant (x direction) are at an angle α of 90° to each other. An implant secured in this position on the operating instrument 60 is suitable in particular for ALIF or ALIF 30° implantation (anterior lumbar interbody fusion), in which the patient lies in the supine position and the implant is introduced from the direction of the abdominal space in order to replace in particular the 5th lumbar vertebra.

In order to ensure good growth of bone through the implant, the threaded spindles 21, 22 are sleeve-shaped and hollow on the inside. In addition, the curved surfaces 34, 35 of the threaded spindles 21, 22 and the curved surfaces 26, 27 of the threaded sleeves 23, 24 have apertures 20, which likewise serve to allow bone to grow through.

The front faces of the threaded sleeves 23, 24 and of the sleeve-shaped threaded spindles 21, 22 are open, i.e. not covered by the upper plate 12 or lower plate 16. The implant thus has two continuous tubular openings which extend from the top face 13 of the upper plate 12 to the underside 17 of the lower plate 16 and can be filled with bone material, and through which growth of bone from the upper adjoining vertebral body to the lower adjoining vertebral body can be achieved.

The upper plate 12 and the lower plate 16 likewise comprise openings and apertures 20 that serve to allow bone to grow through. The basic shape of the plates 12, 16 is oval and similar to an "eight", with outer faces 13, 17 coplanar to each other. Through the size of the bearing surface of the plates 12, 16 on the vertebral bodies, the surface loading of the vertebral bodies is reduced and, in addition, the risk of the implant sinking is reduced.

The thickness of the upper and lower plates 12, 16 is relatively small. Moreover, the sleeves 23, 24 and the spindles 21, 22 are secured in the plates 12, 16 and pass right through these, and each gear consists precisely of one sleeve 23, 24 and one spindle 21, 22. In this way, a compact structure with maximum lift is achieved.

In one variant, the upper plate 12 and/or lower plate 16 can also have a wedge-shaped design, such that the outwardly facing surfaces 13, 17 of the upper plate 12 and lower plate 16 are inclined at an acute angle to each other. In this way, the lordosis shape can be achieved.

In the implant according to the invention, the upper plate 12 forms a fixedly connected part with the threaded spindles 21, 22 and the optionally present guide web 45, and the lower plate 16 likewise forms a fixedly connected part with the portion 43 and the horizontal portion 48. In addition, each threaded sleeve 23, 24 is formed in one piece with the toothed wheel 28, 29 and if appropriate with the drive shaft 30, and the two threaded sleeves 23, 24 are mounted rotatably in the lower plate 16. For this purpose, each threaded sleeve 23, 24 has, on its lower side, an annular collar which is pressed onto the sleeve 23, 24 and which bears underneath the lower plate 16 on the underside of the lower plate 16. The sleeves 23, 24 are thus mounted rotatably in the lower plate, but not vertically adjustably.

The implant is operated with an instrument 60, which is shown in detail in FIG. 6 ff. The instrument 60 serves both for the securing and insertion of the implant and also for the expansion and the fixing of the expansion position.

In order to secure the implant safely on the operating instrument 60 for the subsequent handling, i.e. insertion, positioning, expansion, the instrument 60 comprises two tightening shafts 72, 73 which each comprise a screw thread 66, 74 at their proximal end 62. By means of the screw threads 66, 74, the instrument 60 can be firmly screwed by rotation onto the implant at two adjacent threaded bores 49, 49' on one of the portions 52, 53 or 54 at the distal end 67.

To expand the implant, the instrument 60 comprises a rotation shaft 63, at the proximal end. 62 of which a bevel wheel gear 61 is provided for driving the bevel gear 30. The actuation of the bevel wheel gear 61 takes place via a rotation movement at the distal end 67 of the shaft 63.

The instrument 60 furthermore comprises two tubes 70, 71, which serve to receive and guide the tightening shafts 72, 73 with the screw threads 66, 74. The tubes 70, 71 also serve to receive a screwdriver 80, in order to screw in the screw plugs 78 when the desired expansion position is reached. For this purpose, one of the two tightening shafts 72, 73 with thread 66, 74 is firstly withdrawn from one of the tubes 70, 71, and the screw instrument 80 is pushed into the empty receiving tube 70, 71 and the screw plug 78 is screwed into the threaded bore 49.

The screw instrument 80 consists of a screw shank 84 with knurling and a screw plug tube 83 into the proximal end 62 of which the screw plug 78 is pushed. The screwing takes place through rotation of the screw shank 81.

By means of the screw plug 78, the threaded sleeve 24 is clamped in the desired position relative to the threaded spindle 22.

By screwing the implant to the screw threads 66, 74 of the tightening shafts 72, 73 of the operating instrument 60, not only is a rigid connection between operating instrument 60 and implant and thus a precise insertion achieved, but also at the same time the bevel wheel gear 61 of the operating instrument 60 is brought into engagement with the ring gear 30, such that, after screwing to the implant, and then by rotating the rotation shaft 63 with the bevel wheel gear 61, the implant can be expanded in a defined manner.

The longitudinal axes of the two receiving tubes 70, 71 and of the shafts 63, 72, 73 with the bevel wheel gear 61 and the screw threads 66, 74 extend parallel to one another. The two tubes 70, 71 are connected rigidly to three holders 69, 69', 69", which are located at the proximal end 62, at the distal end 67 and also centrally. The rotation shaft 63 with the bevel wheel gear 61 is mounted rotatably in the holders 69, 69', 69". The holders 69, 69', 69" and the two tubes 70, 71 form a rigid retainer for the rotation shaft 63 with the bevel wheel gear 61 and the tightening shafts 72, 73 with the screw threads 66, 74.

For better positioning of the proximal end 62 of the operating instrument 60 on the horizontal portion 48 with the threaded bores 49, the proximal holder 69 of the operating instrument 60 has, in the proximal direction, a shape corresponding to the angled arrangement of the sub-portions 52, 53, 54 of the horizontal portion 48, namely two positioning limbs 76 (cf. FIGS. 7 and 8) which extend laterally in the proximal direction from the holder 69 at an angle of 120° and which correspond to the profile of the horizontal portion 48, likewise at an angle of 120°, and thus permit simple and precise positioning of the tubes 70, 71 in front of the threaded bores 49, 49' for securing the screw threads 66, 74 of the tightening shafts 72, 73 and the screw plugs 78 with the screw instrument 80.

The rotation shaft 63 with the bevel wheel gear 61 clearly protrudes at the distal end 67 of the operating element 60 such that, during the operation, the physician does not accidentally trigger the screwing instead of the expansion.

By virtue of the small size of the bevel wheel gear 61 and the parallel arrangement of the longitudinal axes of the shafts 63, 72, 73 and of the tubes 70, 71, the operating instrument 60 can be configured in a slender and narrow shape, which facilitates simple and precise insertion from the front, from the rear and also from the side. Such a slender shape of the operating instrument 60 also permits a good view of the operating area.

Since the drive of the implant takes place via the ring gear 30 with the pinion 61 of the operating instrument 60, the operating instrument 60 engages on the xy plane. The longitudinal axis 65 of the operating instrument 60 extends approximately at right angles to the expansion direction (longitudinal axis) of the implant.

The invention claimed is:

1. Expandable implant with an upper plate and a lower plate which serve for anchoring on/in the vertebral support surfaces, and at least two gears for the expansion of the implant, which are coupled to each other via toothed wheels, characterized in that each gear comprises threaded spindles and threaded sleeves, the threaded spindles are connected rigidly to the upper plate, and the threaded sleeves are mounted rotatably in the lower plate, and on one gear a drive shaft is provided, which is connected rigidly to the one threaded sleeve, wherein one of the threaded sleeves, one of the toothed wheels and the drive shaft are formed as a single piece, wherein a force acting on the drive shaft of an operating instrument can be transferred to the gear by means of the drive shaft, wherein the implant comprises means for rigidly securing, screwing or fixing the operating instrument on the implant, and wherein the drive shaft is a ring gear.

2. Implant according to claim 1, characterized in that the one or more means for securing, screwing or rigidly fixing the operating instrument are rigidly connected to the lower plate, in which the threaded sleeve with the drive shaft is mounted.

3. Implant according to claim 1, characterized in that the distance between the drive shaft of the implant and the means for securing the operating instrument is not modifiable.

4. Implant according to claim 1, characterized in that the means for securing, screwing or fixing in the implant are bores, in particular threaded bores.

5. Implant according to claim 1, characterized in that the upper plate and the lower plate and/or the threaded spindles and/or the threaded sleeves have apertures and/or the front faces of the threaded spindles and of the threaded sleeves are open.

6. Implant according to claim 1, characterized in that each threaded sleeve is formed in one piece with the toothed wheel and, if appropriate, the drive shaft.

7. Implant according to claim 1, characterized in that each threaded sleeve has, on its underside, an annular collar which is fixedly connected to the sleeve and which bears on the underside of the lower plate.

8. Implant according to claim 1, characterized in that an inner curved surface of the threaded sleeves is provided with threads, which form the spindle nuts for the outer threads of the threaded spindles.

9. Implant according to claim 1, characterized in that the directions of rotation of the threaded sleeves are different.

10. Implant according to claim 1, characterized in that the implant has a plurality of differently oriented sub-portions for securing the operating instrument.

11. Operating instrument for an implant according claim 1, which operating instrument has a drive shaft for actuation of the drive shaft of the implant, and means for securing to the corresponding securing means of the implant.

12. Operating instrument according to claim 11, characterized in that the securing means are screw threads, in particular outer threads at the proximal end of a tightening shaft.

13. Operating instrument according to claim 11, characterized in that the drive shaft is a bevel wheel gear at the proximal end of a rotation shaft.

14. Operating instrument according to claim 11, characterized in that the operating instrument comprises a retainer with tubes and holders, wherein the longitudinal axes of the tubes extend parallel to each other, and the tubes serve to receive the tightening shafts and/or a screw instrument.

* * * * *